(12) United States Patent
Beeckler et al.

(10) Patent No.: US 8,123,745 B2
(45) Date of Patent: Feb. 28, 2012

(54) ABLATION CATHETER WITH OPTICALLY TRANSPARENT, ELECTRICALLY CONDUCTIVE TIP

(75) Inventors: Christopher Beeckler, Brea, CA (US); Chad Allen Lieber, Chino Hills, CA (US); Shiva Sharareh, Laguna Niguel, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 263 days.

(21) Appl. No.: 11/824,038

(22) Filed: Jun. 29, 2007

(65) Prior Publication Data
US 2009/0005773 A1  Jan. 1, 2009

(51) Int. Cl.
*A61B 18/14* (2006.01)
(52) U.S. Cl. .......................... 606/41; 600/374
(58) Field of Classification Search ............... 606/41, 606/46–47; 600/160, 175, 178, 182; 607/119, 607/122
See application file for complete search history.

(56) References Cited

U.S. PATENT DOCUMENTS
5,391,199 A  2/1995  Ben-Haim
(Continued)

FOREIGN PATENT DOCUMENTS
WO  WO 95/02995  2/1995
(Continued)

OTHER PUBLICATIONS
European Search Report, mailed Sep. 25, 2008 for European Application No. EP 08252237.6, 6 pgs.

*Primary Examiner* — Michael Peffley
*Assistant Examiner* — Benjamin Lee
(74) *Attorney, Agent, or Firm* — Christie, Parker & Hale, LLP

(57) ABSTRACT

A catheter enables real-time light measurements, for example, without limitation, diffuse reflectance, fluorescence, etc., from biological materials, such as tissue (including blood), while performing RF ablation. The catheter tip design isolates illumination and collection paths such that light exits the catheter tip and travels through the tissue of interest (e.g., cardiac tissue or blood) before returning to the catheter tip. Such a design advantageously avoids saturation of the optical detector, and ensures diffusion of the illumination light within the medium of interest. The catheter has a catheter body and a tip electrode. The tip electrode has an exterior shell, an inner layer of diffuse material and a hollow cavity, wherein the inner layer is configured to transmit light outside the tip electrode to a tissue via a set of illumination openings in the shell wall and the hollow cavity is configured to receive light from the tissue via a set of collection openings in the shell wall and the inner layer. An inner surface of the inner layer has a reflective coating to isolate light injected into the inner layer from light collected in the hollow cavity. There are a first optical waveguide extending between the catheter body and the tip electrode to inject light into the inner layer and illuminate the tissue, and a second optical waveguide extending between the catheter body and the tip electrode to collect the recaptured light in the hollow cavity.

16 Claims, 9 Drawing Sheets

U.S. PATENT DOCUMENTS

| | | |
|---|---|---|
| 5,443,489 A | 8/1995 | Ben-Haim |
| 5,480,422 A | 1/1996 | Ben-Haim |
| 5,546,951 A | 8/1996 | Ben-Haim |
| 5,558,091 A | 9/1996 | Acker et al. |
| 5,568,809 A | 10/1996 | Ben-haim |
| 5,964,757 A | 10/1999 | Ponzi |
| 6,064,908 A | 5/2000 | Muller et al. |
| 6,394,949 B1* | 5/2002 | Crowley et al. ............... 600/127 |
| 6,405,067 B1* | 6/2002 | Mest et al. .................... 600/374 |
| 6,602,242 B1 | 8/2003 | Fung et al. |
| 6,918,906 B2* | 7/2005 | Long ............................. 606/41 |
| 2003/0144656 A1* | 7/2003 | Ocel et al. ...................... 606/41 |
| 2003/0228085 A1* | 12/2003 | Zuluaga et al. ................ 385/15 |
| 2004/0111141 A1* | 6/2004 | Brabec et al. ................. 607/119 |
| 2005/0203604 A1* | 9/2005 | Brabec et al. ................. 607/122 |
| 2006/0030844 A1* | 2/2006 | Knight et al. ................... 606/41 |
| 2006/0122587 A1 | 6/2006 | Sharareh |
| 2007/0066972 A1* | 3/2007 | Ormsby et al. ................. 606/41 |
| 2007/0141345 A1 | 6/2007 | Rinzler et al. |
| 2008/0039770 A1* | 2/2008 | Francis et al. ................. 604/20 |
| 2009/0131931 A1* | 5/2009 | Lee et al. ....................... 606/41 |

FOREIGN PATENT DOCUMENTS

| | | |
|---|---|---|
| WO | WO 2006/127241 | 11/2006 |
| WO | WO 2007/146995 | 12/2007 |

* cited by examiner

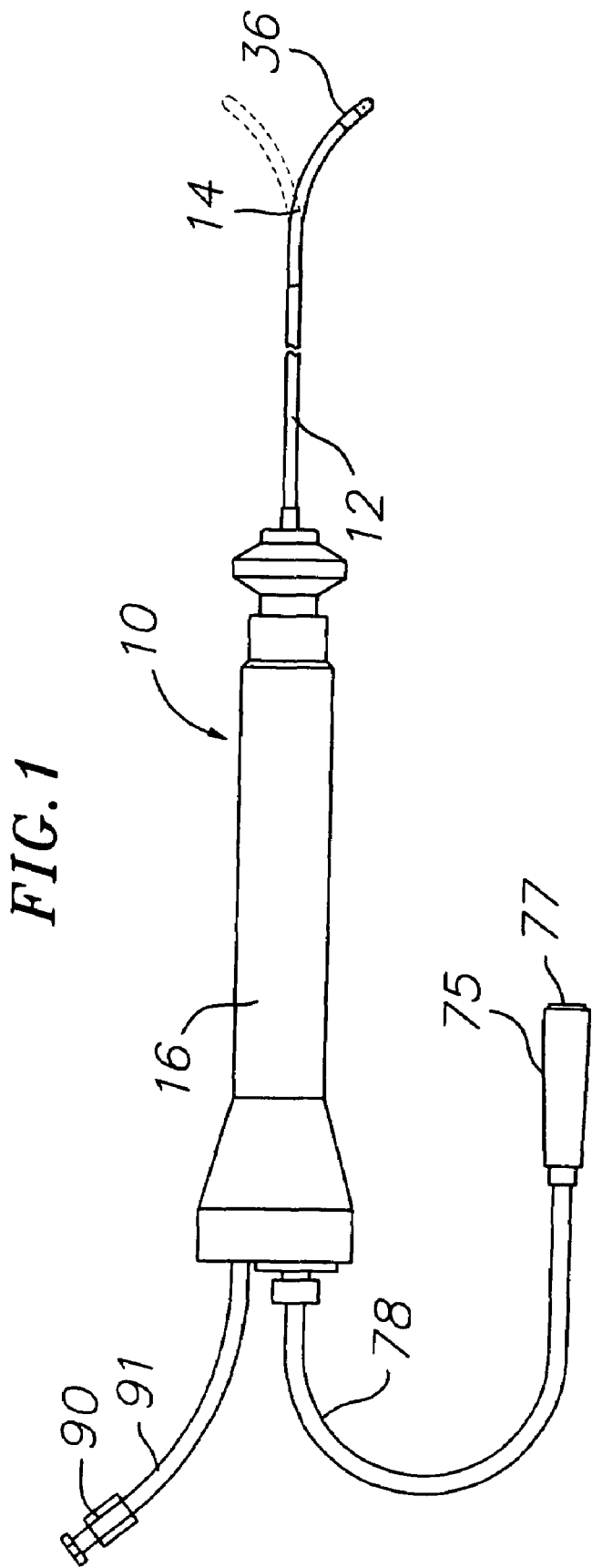

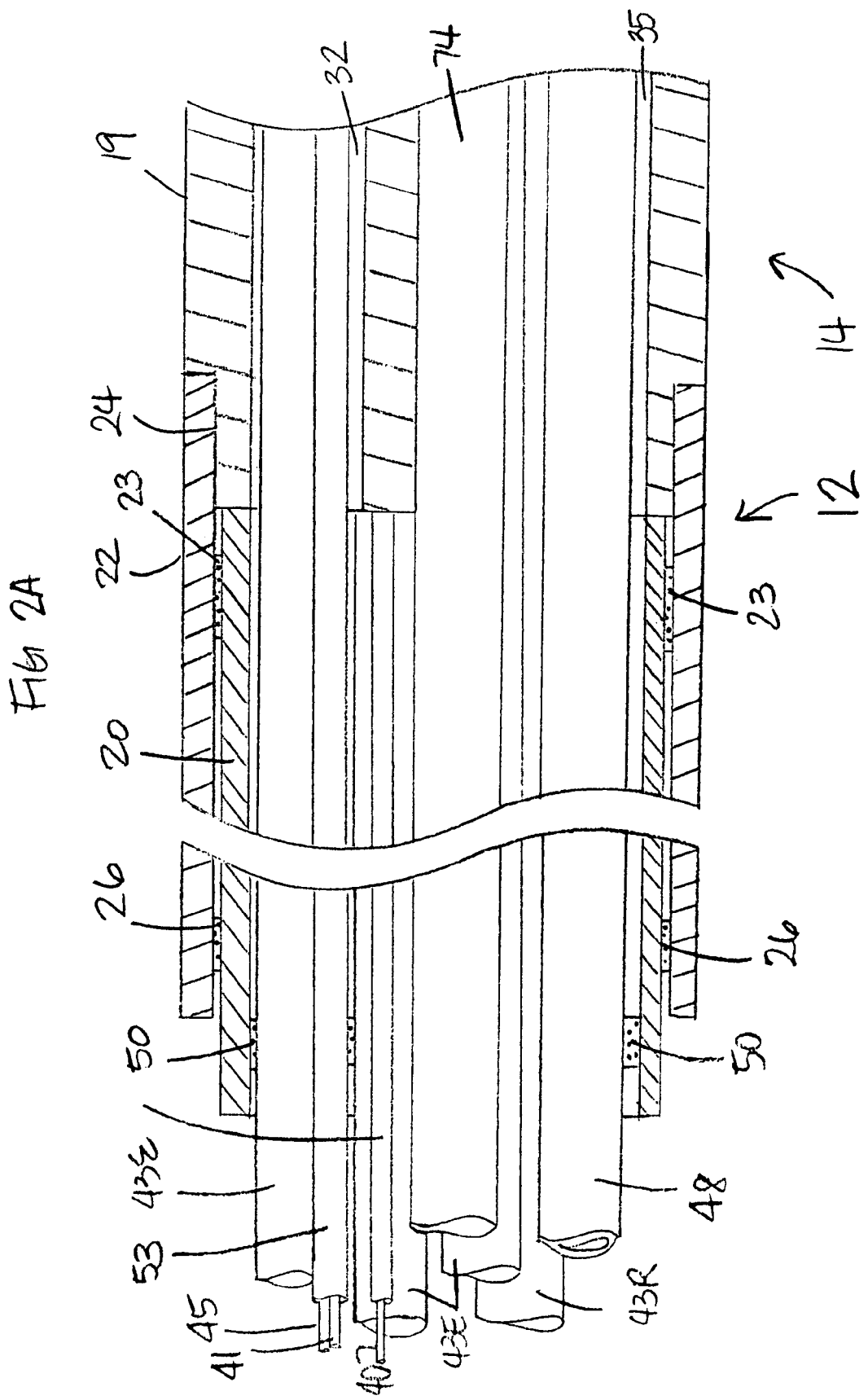

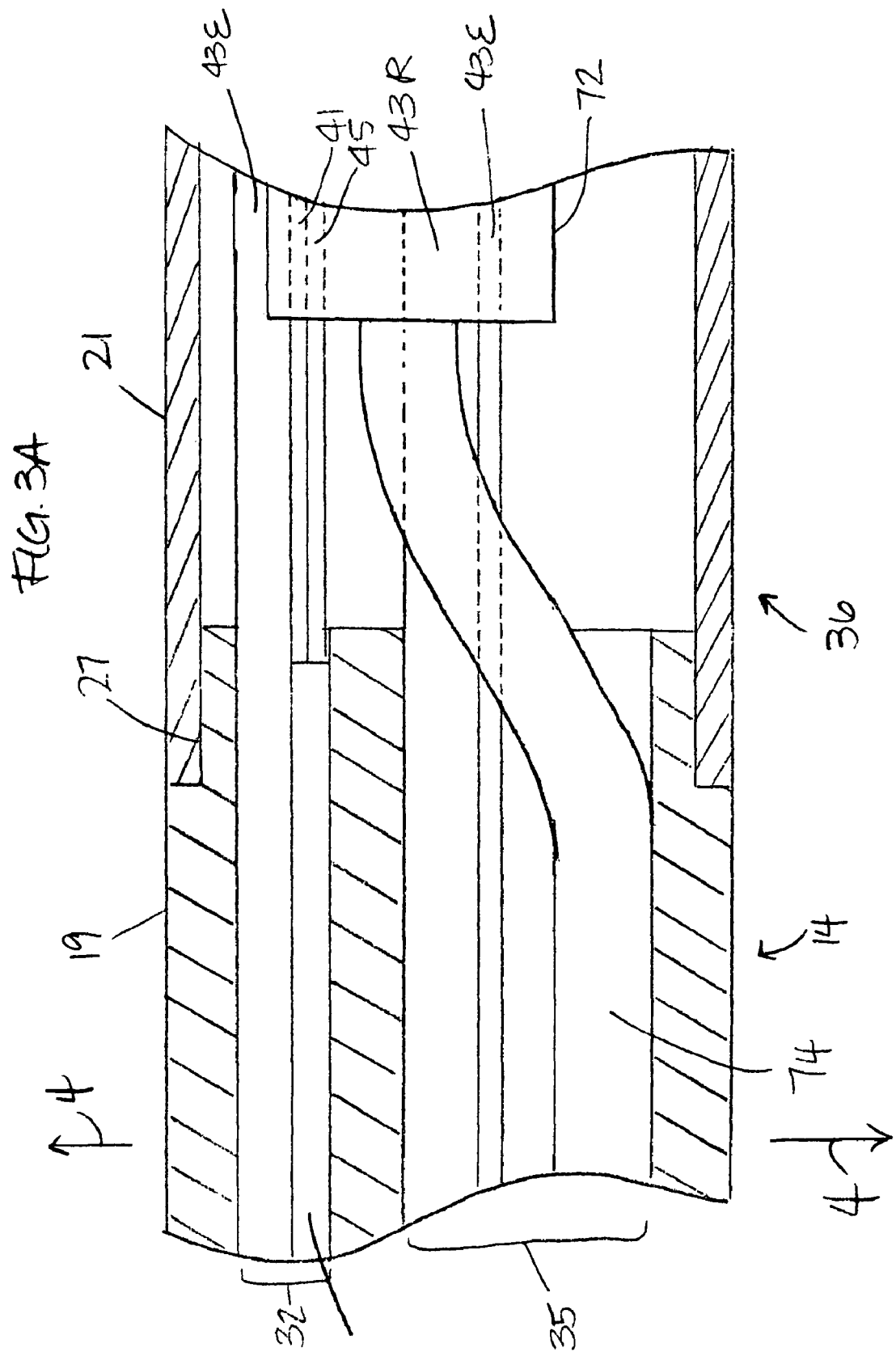

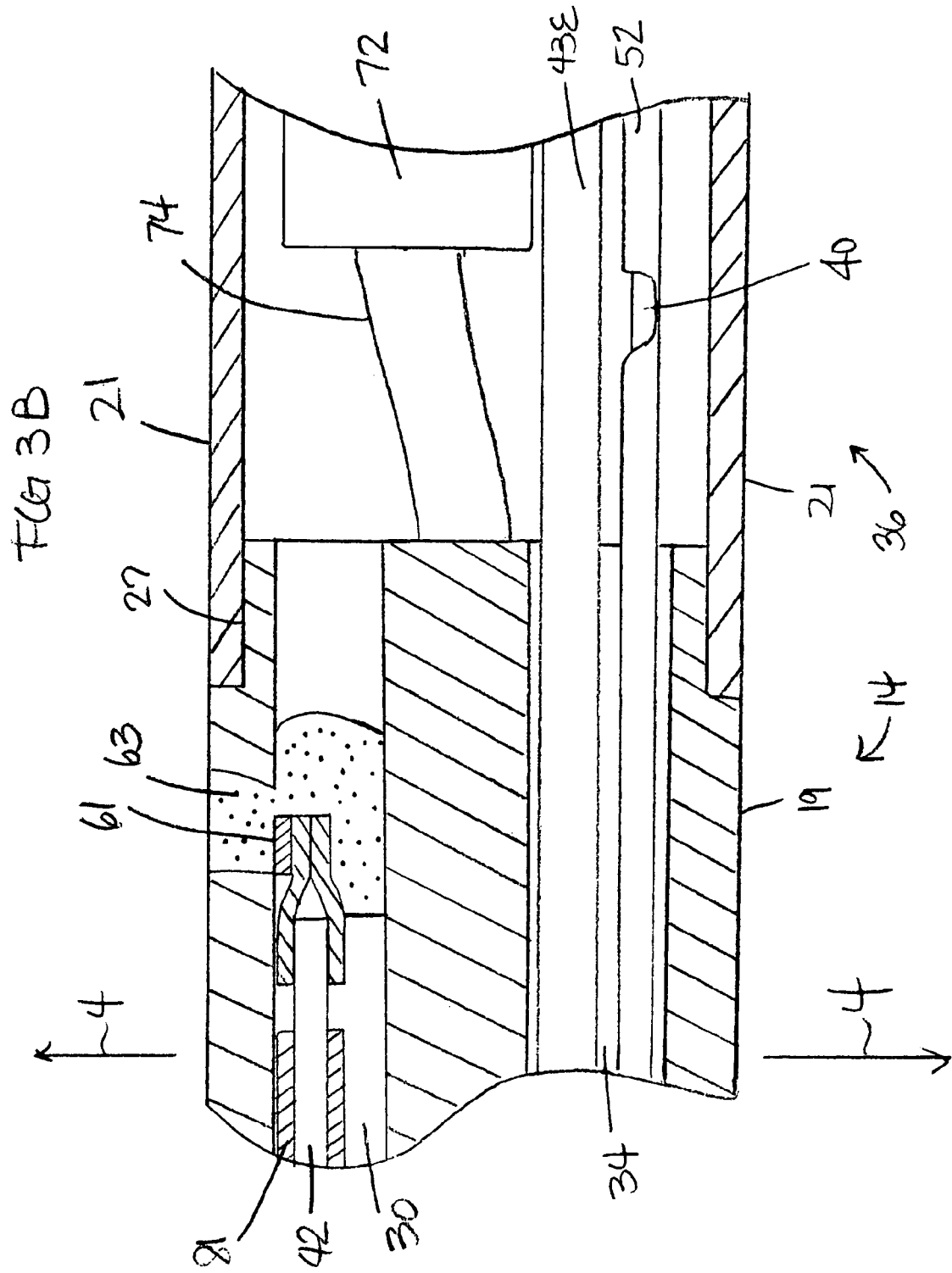

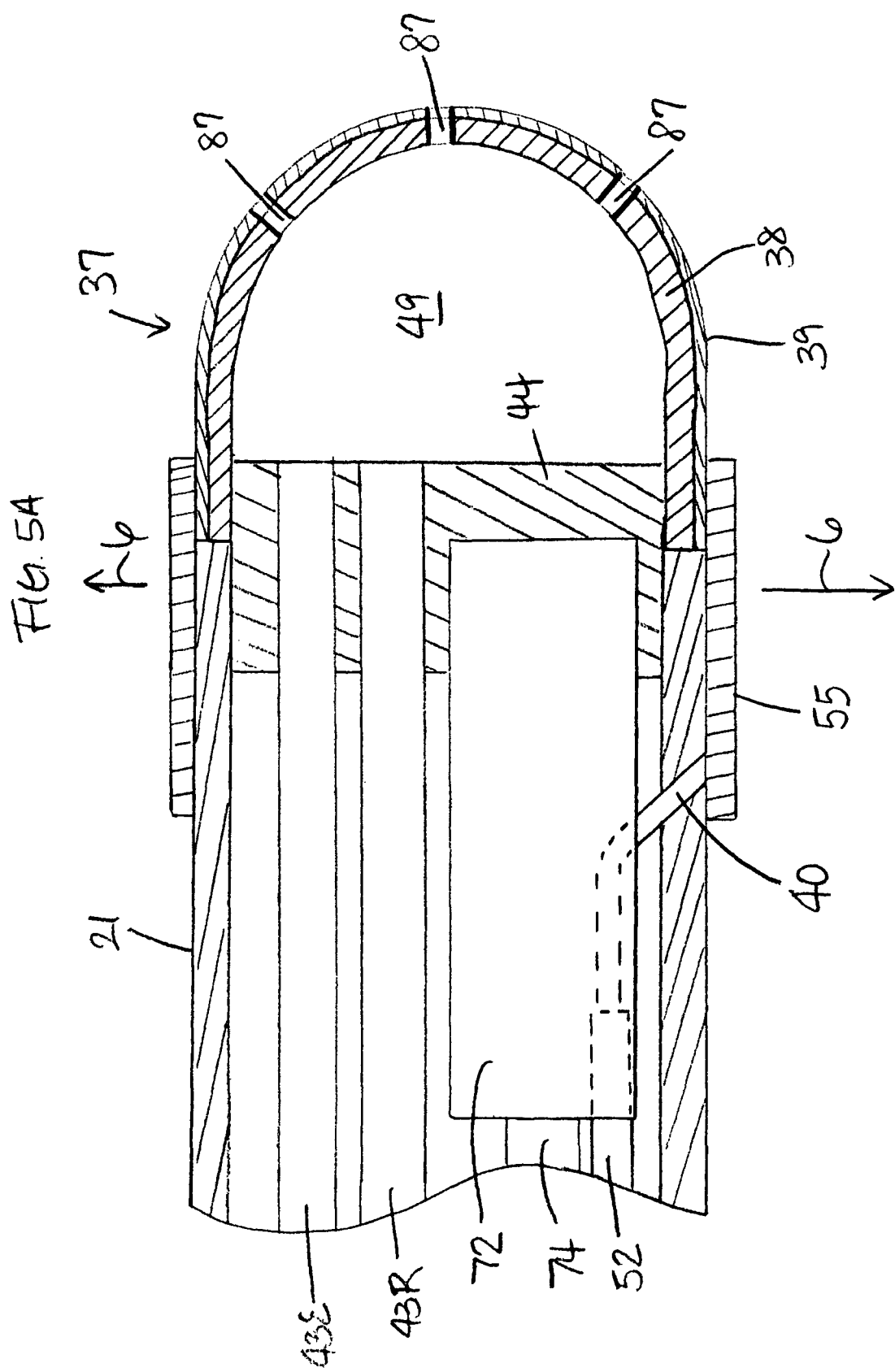

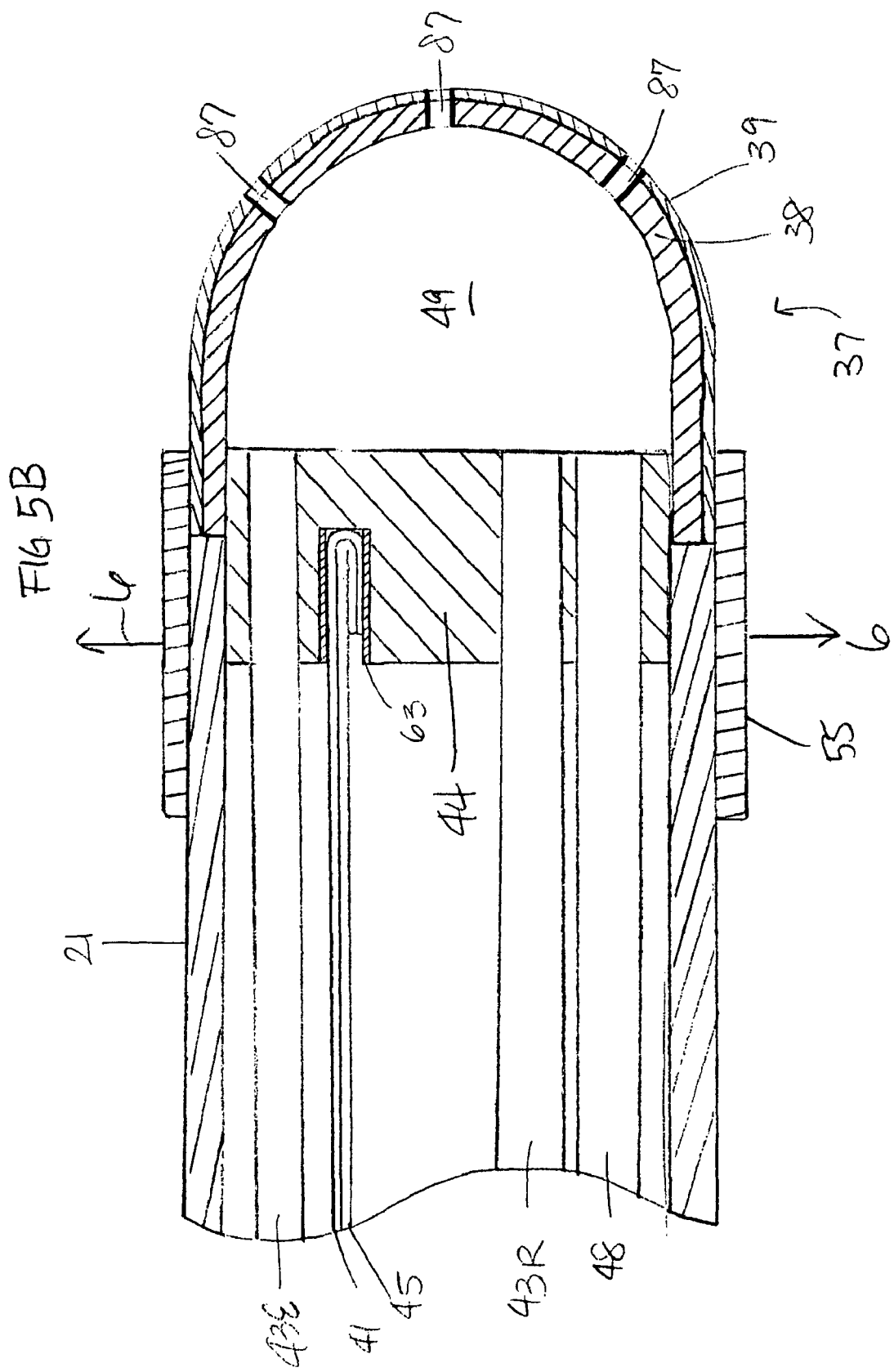

ABLATION CATHETER WITH OPTICALLY TRANSPARENT, ELECTRICALLY CONDUCTIVE TIP

FIELD OF INVENTION

The present invention relates to ablation catheters, and in particular to ablation catheters with optical monitoring of tissue.

BACKGROUND

For certain types of minimally invasive medical procedures, real time information regarding the condition of the treatment site within the body is unavailable. This lack of information inhibits the clinician when employing catheter to perform a procedure. An example of such procedures is tumor and disease treatment in the liver and prostate. Yet another example of such a procedure is surgical ablation used to treat atrial fibrillation. This condition in the heart causes abnormal electrical signals, known as cardiac arrhythmias, to be generated in the endocardial tissue resulting in irregular beating of the heart.

The most frequent cause of cardiac arrhythmias is an abnormal routing of electricity through the cardiac tissue. In general, most arrhythmias are treated by ablating suspected centers of this electrical misfiring, thereby causing these centers to become inactive. Successful treatment, then, depends on the location of the ablation within the heart as well as the lesion itself. For example, when treating atrial fibrillation, an ablation catheter is maneuvered into the right or left atrium where it is used to create ablation lesions in the heart. These lesions are intended to stop the irregular beating of the heart by creating non-conductive barriers between regions of the atria that halt passage through the heart of the abnormal electrical activity.

The lesion should be created such that electrical conductivity is halted in the localized region (transmurality), but care should be taken to prevent ablating adjacent tissues. Furthermore, the ablation process can also cause undesirable charring of the tissue and localized coagulation, and can evaporate water in the blood and tissue leading to steam pops.

Currently, lesions are evaluated following the ablation procedure, by positioning a mapping catheter in the heart where it is used to measure the electrical activity within the atria. This permits the physician to evaluate the newly formed lesions and determine whether they will function to halt conductivity. It if is determined that the lesions were not adequately formed, then additional lesions can be created to further form a line of block against passage of abnormal currents. Clearly, post ablation evaluation is undesirable since correction requires additional medical procedures. Thus, it would be more desirable to evaluate the lesion as it is being formed in the tissue.

A known method for evaluating lesions as they are formed is to measure electrical impedance. Biochemical differences between ablated and normal tissue can result in changes in electrical impedance between the tissue types. Although impedance is routinely monitored during electrophysiologic therapy, it is not directly related to lesion formation. Measuring impedance merely provides data as to the location of the tissue lesion but does not give qualitative data to evaluate the effectiveness of the lesion.

Another approach is to measure the electrical conductance between two points of tissue. This process, known as lesion pacing, can also determine the effectiveness of lesion therapy. This technique, however, measures the success or lack thereof from each lesion, and yields no real-time information about the lesion formation.

Thus, there is a need for a catheter capable of measuring characteristics of lesion formation in real-time, and doing so with optical imaging, whether the catheter is parallel, perpendicular or at an angle to the tissue. It would be desirable for the catheter to be adapted for ablation as well. To that end, the catheter tip should be transparent yet also electrically conductive so that optical data can be sensed by the catheter tip during, before or after ablation.

There are available many transparent, electrical conductors but each has its limitations. Carbon nanotube film is one such transparent, electrical conductor. Carbon nanotubes were discovered in or about 1991, but their existence had been suspected earlier based on mathematical calculations. Carbon nanotubes have a large length to diameter ratio and thus can be seen as nearly one-dimensional forms of fullerenes. They possess interesting electrical, mechanical and molecular properties. There are single walled nanotubes (SWNT) where the length to diameter ratio is about 1000. There are multi-walled nanotubes (MWNT) with multiple concentric SWNTs with different diameters. MWNTs have different lengths and diameters from SWNTs and they also have different properties.

It is now possible to fabricate ultrathin, transparent, optically homogenous, electrically conducting films of carbon nanotubes and to transfer those films onto various substrates. The challenge had been to deposit nanotubes in a layer thin enough to be optically transparent while maintaining electrical contract through the layer. The films exhibit optical transmittance in the visible spectrum and the infrared. In the near-to-mid infrared, carbon nanotube films have been shown to have good to high transparency for given electrical conductivity of most things currently available. Even in the visible spectrum, the electrical conductivity of nanotube films for given transparency is comparable to commercially available indium tin oxide (ITO) which is another substance that has electrical conductivity and optical transparency.

Accordingly, it would therefore be desirable to provide a catheter that is adapted for optical imaging and electrical conductivity such as for ablation, having a tip that is optically omnidirectional and constructed of carbon nanotube film. Such a catheter may also be adapted for ultrasound imaging concurrently with electrical ablation therapy.

SUMMARY OF THE INVENTION

The present invention is directed to a catheter that ablates and enables real-time omnidirectional light measurements, for example, without limitation, diffuse reflectance, fluorescence, etc., from biological materials, such as tissue (including blood). The catheter tip design employs carbon nanotube film which in sufficiently thin form offers electrical conduction and optical transparency. The light recaptured from the tissue through the film-covered electrode tip conveys tissue parameters that can be evaluated using optical spectroscopy. These parameters include, without limitation, lesion formation, depth of penetration of lesion, and cross-sectional area of lesion, formation of char during ablation, recognition of char during ablation, recognition of char from non-charred tissue, formation of coagulum around the ablation site, differentiation of coagulated from non-coagulated blood, differentiation of ablated from healthy tissue, tissue proximity, evaluation of tissue health, status, and disease state, and recognition of steam formation in the tissue for prevention of steam pop.

In one embodiment, a catheter has a catheter body and a tip electrode that includes an optically transmissive shell coated with a carbon nanotube film. It is contemplated that the optically transmissive shell is adapted for optical illumination and collection, and the carbon nanotube film is adapted for tissue ablation. Moreover, it is contemplated that the shell is generally shaped as a dome defining a cavity and that the shell is optically transparent. The film is also optically transmissive if not optically transparent. The cavity is illuminated by at least one emitting optical fiber and light entering the cavity from tissue is received by at least one receiving optical fiber which communicates with an optical processing system.

In a more detailed embodiment, a catheter has a catheter body and a tip electrode with an optically transparent shell and an electrically conductive and optically transparent film on the shell. The shell defines a cavity to receive light from the tissue and the film is adapted to ablate tissue. A first optical waveguide extends into the cavity to provide light and a second optical waveguide extends into the cavity to collect light. The tip electrode is adapted for RF ablation and the catheter may also include an irrigation tubing to deliver fluid to the cavity and through openings in the shell to reach outside the tip electrode. The catheter may include a deflectable intermediate section between the catheter body and the tip electrode, and a temperature sensor configured to sense temperature in the tip electrode. There may also be an electromagnetic location sensor configured to sense location of the tip electrode.

Advantageously, the light used to monitor and assess the tissue (or a lesion formed in the tissue) is generally not affected by the portion of the electromagnetic radiation used for ablation. Moreover, the bandwidth used for monitoring and assessing also transmits through blood with minimal attenuations. The fiber optics are used and disposed in the catheter in a manner that avoids contact with tissue, which can increase the operative lifetime of the catheter and minimize damages caused by abrasion to the fiber optics. Furthermore, the alignment plug in the tip electrode secures the fiber optic cables with minimal bend or strain but increased angular coverage, which can minimize fiber optics breakage during assembly and use, as well as reduce nonlinear optical effects caused by orientation of the fiber optics. In addition, the use of fiber optics to emit and receive light is a generally temperature neutral process that adds little if any measurable heat to surrounding blood or tissue.

BRIEF DESCRIPTION OF THE DRAWINGS

These and other features and advantages of the present invention will be better understood by reference to the following detailed description when considered in conjunction with the accompanying drawings wherein:

FIG. 1 is a side view of an embodiment of the catheter of the present invention.

FIG. 2A is a side cross-sectional view of an embodiment of a catheter according to the invention, including the junction between a catheter body and an intermediate section, taken along a first diameter.

FIG. 3A is a side cross-sectional view of an embodiment of a catheter according to the invention, including the junction between the intermediate section and a plastic housing, taken along the first diameter.

FIG. 3B is a side cross-sectional view of an embodiment of a catheter according to the invention, including the junction between the intermediate section and the plastic housing, taken generally along the second diameter.

FIG. 5A is a side cross sectional view of an embodiment of a catheter according to the invention, including a junction between the plastic housing and a tip electrode, taken generally along diameter 5A-5A as shown in FIG. 6.

FIG. 5B is a side cross-sectional view of an embodiment of a catheter body according to the invention, including the junction between the plastic housing and the tip electrode, taken generally along diameter 5B-5B as shown in FIG. 6.

DETAILED DESCRIPTION OF THE INVENTION

Figure 2B:
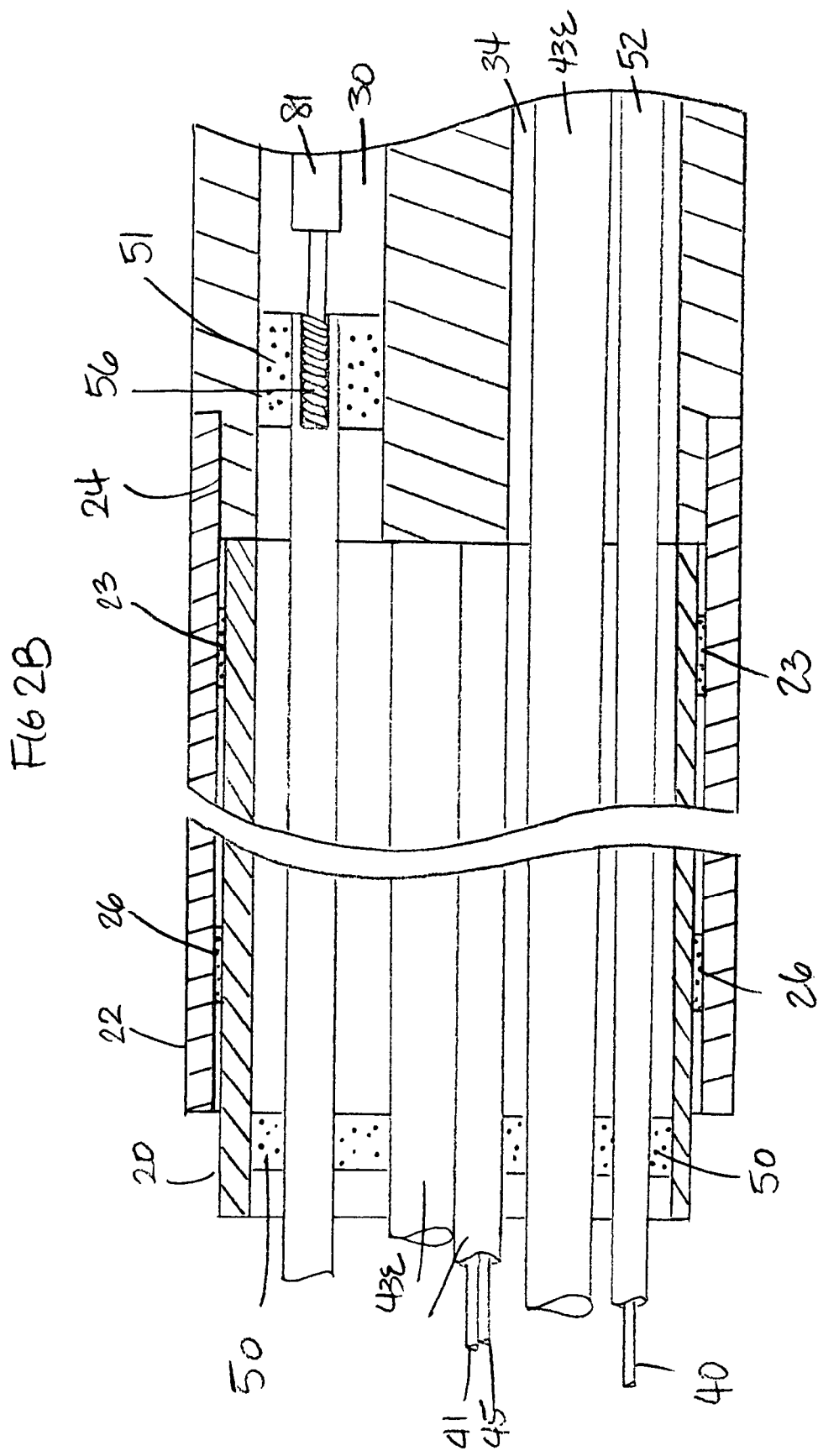
FIG. 2B is a side cross-sectional view of an embodiment of a catheter according to the invention, including the junction between the catheter body and the intermediate section, taken along a second diameter generally perpendicular to the first diameter of FIG. 2A.

As shown in FIGS. 1-6, a catheter 10 of the present invention comprises an elongated catheter body 12 having proximal and distal ends, a deflectable (uni- or bi-directionally) intermediate section 14 at the distal end of the catheter body 12, a tip section 36 at the distal end of the intermediate section, and a control handle 16 at the proximal end of the catheter body 12.

With additional reference to FIGS. 2A and 2B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A construction comprises an outer wall 22 made of an extruded plastic. The outer wall 22 may comprise an imbedded braided mesh of stainless steel or the like to increase torsional stiffness of the catheter body 12 so that, when the control handle 16 is rotated, the catheter body 12, the intermediate section 14 and the tip section 36 of the catheter 10 will rotate in a corresponding manner.

Extending through the single lumen 18 of the catheter body 12 are components, for example, lead wire 40 and thermocouple wires 41, 45 protected by a sheath 53, optical fibers 43, an irrigation tube 48, a compression coil 56 through which a puller wire 42 extends, and an electromagnetic sensor cable 74. A single lumen catheter body can be preferred over a multi-lumen body because it has been found that the single lumen body permits better tip control when rotating the catheter. The single lumen permits the various components such as the lead wire, thermocouple wires, infusion tube, and the puller wire surrounded by the compression coil to float freely within the catheter body. If such wires, tube and cables were restricted within multiple lumens, they tend to build up energy when the handle is rotated, resulting in the catheter body having a tendency to rotate back if, for example, the handle is released, or if bent around a curve, to flip over, either of which are undesirable performance characteristics.

The outer diameter of the catheter body 12 is not critical, but is preferably no more than about 8 french, more preferably 7 french. Likewise the thickness of the outer wall 22 is not critical, but is thin enough so that the central lumen 18 can accommodate the aforementioned components. The inner surface of the outer wall 22 may be lined with a stiffening tube 20, which can be made of any suitable material, such as polyimide or nylon. The stiffening tube 20, along with the braided outer wall 22, provides improved torsional stability while at the same time minimizing the wall thickness of the catheter, thus maximizing the diameter of the central lumen 18. The outer diameter of the stiffening tube 20 is about the same as or slightly smaller than the inner diameter of the outer wall 22. Polyimide tubing may be preferred for the stiffening tube 20 because it may be very thin walled while still providing very good stiffness. This maximizes the diameter of the central lumen 18 without sacrificing strength and stiffness.

The catheter may have an outer wall 22 with an outer diameter of from about 0.090 inch to about 0.104 inch and an inner diameter of from about 0.061 inch to about 0.075 inch and a polyimide stiffening tube 20 having an outer diameter of from about 0.060 inch to about 0.074 inch and a wall thickness of about 0.001-0.005 inch.

Figure 4:
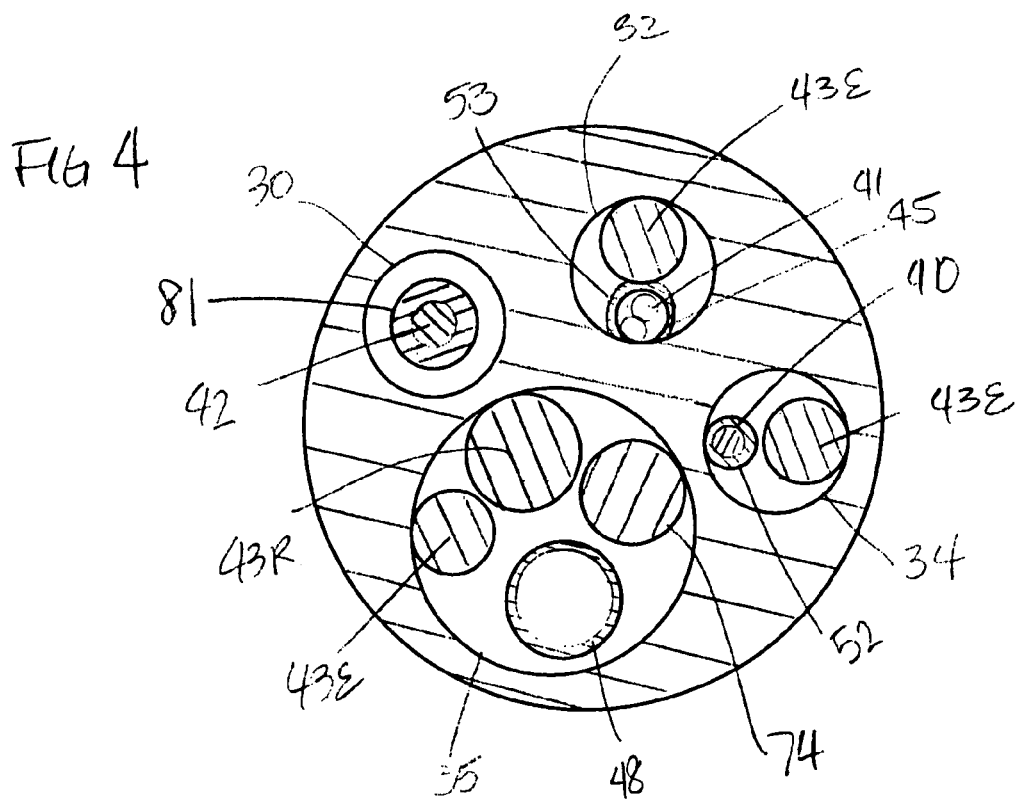
FIG. 4 is a longitudinal cross-sectional view of an embodiment of an intermediate section of FIGS. 3A and 3B, taken generally along line 4-4.

Referring also to FIGS. 3A, 3B and 4, the intermediate section 14 distal of the catheter body 12 comprises a shorter section of tubing 19 having multiple lumens. The tubing 19 is made of a suitable non-toxic material that is preferably more flexible than the catheter body 12. A suitable material for the tubing 19 is braided polyurethane with low to medium durometer plastic. The outer diameter of the intermediate section 14, like that of the catheter body 12, is preferably no greater than about 8 french, more preferably 7 french. The size and number of the lumens is not critical. In an embodiment, the intermediate section 14 has an outer diameter of about 7 french (0.092 inch). The tubing 19 has a first off-axis lumen 30, a second off-axis lumen 32 and a third off-axis lumen 34 that are generally about the same size, each having a diameter of from about 0.020 inch to about 0.024 inch, preferably 0.022 inch, along with a fourth off-axis lumen 35, having a larger diameter of from about 0.032 inch to about 0.038 inch, preferably 0.036 inch.

Referring back to FIGS. 2A and 2B, the catheter body 12 may be attached to the intermediate section 14 formed with an outer circumferential notch 24 configured in the proximal end of the tubing 19 that receives the inner surface of the outer wall 22 of the catheter body 12. The intermediate section 14 and catheter body 12 are attached by glue or the like. Before the intermediate section 14 and catheter body 12 are attached, the stiffening tube 20 is inserted into the catheter body 12. The distal end of the stiffening tube 20 is fixedly attached near the distal end of the catheter body 12 by forming a glue joint 23 with polyurethane glue or the like. Preferably a small distance, e.g., about 3 mm, is provided between the distal end of the catheter body 12 and the distal end of the stiffening tube 20 to permit room for the catheter body 12 to receive the notch 24 of the intermediate section 14. If no compression coil is used, a force is applied to the proximal end of the stiffening tube 20, and, while the stiffening tube 20 is under compression, a first glue joint (not shown) is made between the stiffening tube 20 and the outer wall 22 by a fast drying glue, e.g. cyanoacrylate. Thereafter a second glue joint 26 is formed between the proximal ends of the stiffening tube 20 and outer wall 22 using a slower drying but stronger glue, e.g., polyurethane.

If desired, a spacer can be located within the catheter body between the distal end of the stiffening tube and the proximal end of the tip section. The spacer provides a transition in flexibility at the junction of the catheter body and intermediate section, which allows this junction to bend smoothly without folding or kinking. A catheter having such a spacer is described in U.S. patent application Ser. No. 08/924,616, entitled "Steerable Direct Myocardial Revascularization Catheter", the entire disclosure of which is incorporated herein by reference.

Extending from the distal end of the intermediate section 14 is the tip section 36 that includes a tip electrode 37 and a plastic housing 21 as shown in FIGS. 5A and 5B. The plastic housing 21 connects the tip electrode 37 and the tubing 19 and provides components that extend through its lumen with housing and/or transitional space, as discussed further below. The plastic housing 21 is preferably made of polyetheretherketone (PEEK) and may be about 1 cm long. Its proximal end is received in an outer circumferential notch 27 (FIGS. 3A and 3B) formed in the distal end of the tubing 19 of the intermediate section 14. The intermediate section 14 and the plastic housing 21 are attached by glue or the like. Components such as wires, cables and tube segments that extend between the intermediate section 14 and the tip electrode 38 may help keep the tip electrode in place.

The dome tip electrode 37 has an open proximal end that is in communication with a generally hollow distal portion or cavity 49. The tip electrode includes an optically-transmissive if not optically-transparent shell 38 of generally uniform thickness on which there is deposited electrically conductive carbon nanotube film or coating 39. The tip electrode also includes a press-fit plug or alignment member 44 is positioned at or near the proximal end of the shell.

The shell 38 is configured with a dome or similar shape at its distal end to facilitate omnidirectional illumination and collection of light. Its exterior with the film 39 thereon is configured atraumatically and adapted for contact with tissue. The shell is configured with a plurality of through-holes or openings 87 for irrigation/infusion purposes. The shell is formed from any suitable material that is optically transparent, including glass or plastics. And because the carbon nanotube film 39 is suitably thin for optical transparency, the shell of the tip electrode functions as an omnidirectional illuminator and collector. Accordingly, the dome tip electrode 37 is configured for ablation and illumination and collection of light from tissue for optical spectroscopy. For the latter functions, optical fibers are in communication with the cavity 49, as explained in detail further below.

Figure 6:
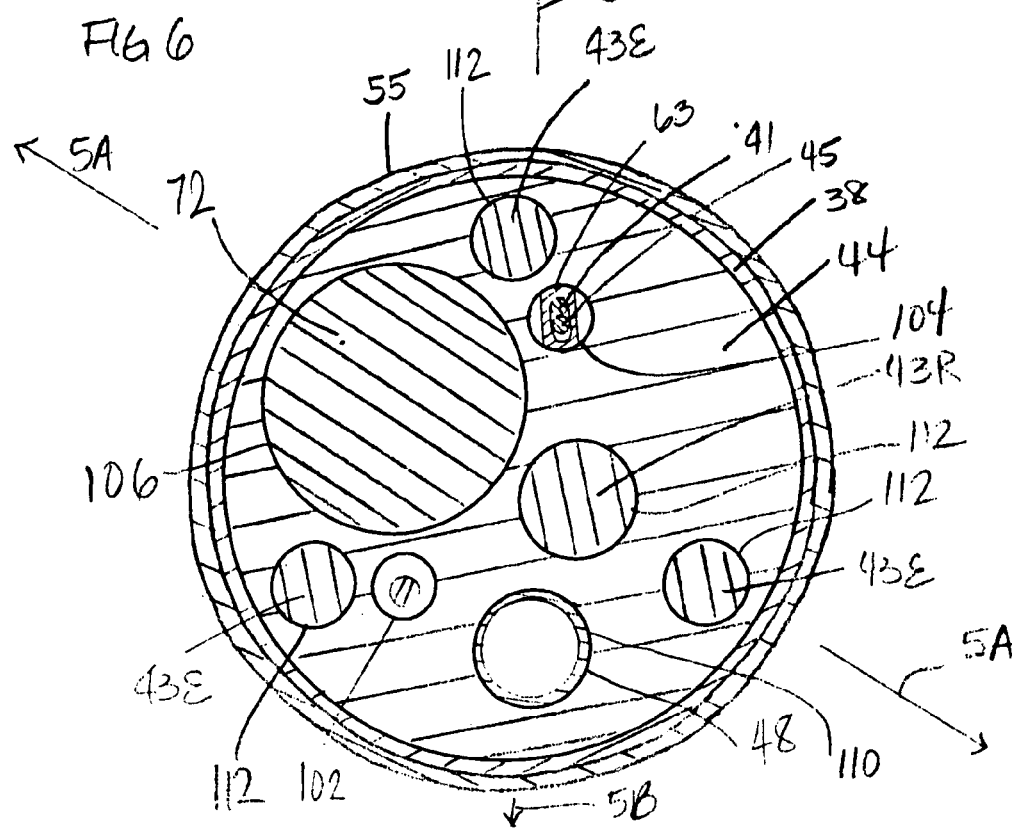
FIG. 6 is a longitudinal cross-sectional view of an embodiment of a plastic housing of FIGS. 4A and 4B, taken along line 6-6.

The plug 44 has a generally elongated cylindrical configuration having a predetermined length and a generally circular cross-section. A distal portion of the plug 44 is press fitted into the open proximal end of the tip electrode 37 to seal the hollow cavity 49, while a proximal portion of the plug 44 extends proximally from the tip electrode 37 for attachment to the housing 21. As shown in FIG. 6, various blind holes and passages are provided in the plug to allow components to be anchored to the plug or to pass through to the hollow cavity 49. In the illustrated embodiment, there are blind holes 102, 104 and 106 in which distal ends of the lead wire 40, the thermocouple wires 41 and 45 and the location sensor 72 are anchored, respectively. There are also passages 112 116 through which the optical fibers 43 extend, and a passage 110 through which the irrigation tube segment 48 extends. The portions of the components extending through the passages in the plug are securely fixed in the passages by glue, adhesive or the like. The passages help align, stabilize and secure the various components extending through the plug 44.

In accordance with a feature of the present invention, the catheter 10 is adapted to facilitate optically-based real-time assessment of ablation tissue characteristics, including without limitation, lesion formation, depth of penetration of the lesion, cross-sectional area of the lesion, formation of char during ablation, recognition of char during ablation, differentiation of char from non-charred tissue, formation of coagulum around the ablation site, differentiation of coagulated from non-coagulated blood, differentiation of ablated from healthy tissue, tissue proximity, and recognition of steam formation in the tissue for prevention of steam pop. These assessments are accomplished by measuring the light intensity at one or more wavelengths that is recaptured at the catheter resulting from the light radiated from the catheter tip onto ablated tissue. In that regard, the optical fibers 43E extend into the tip electrode 37 to transmit light to the tip electrode and the optical fiber 43R collects light from the tissue for such optically based real-time tissue assessment.

The fiber optic cables 43 are protectively housed in the catheter from the control handle 16 to the tip section 36. As shown in FIGS. 2B and 4, they extend through the central lumen 18 of the catheter 12 and the lumens 32, 34 and 35 of the intermediate section 14. They extend through the plastic housing 21 and into the tip electrode 37 via the passages 112 in the plug 44. The passages help minimize stress on the fibers 43 in their transition between the intermediate section 14 and the tip electrode 37.

In the disclosed embodiment, there are three emitting fibers 43E and one receiving fiber 43R. The fibers 43E function as a light emitters by transmitting light to the tip electrode 37 from a remote light source. The fiber 43R functions as a light receiver by collecting light from the hollow cavity 49 in the tip electrode 37. Each of the cables 43T and 43R may be a single fiber optic cable or fiber bundles. They may be single mode (also known as mono-mode or uni-mode), multi-mode (with step index or graded index) or plastic optical fiber (POF), depending on a variety of factors, including but not limited to transmission rate, bandwidth of transmission, spectral width of transmission, distance of transmission, diameter of cable, cost, optical signal distortion tolerance and signal attenuation, etc. Moreover, light delivery and collection may be accomplished with other devices, such as air-core fibers, hollow waveguides, liquid waveguides and the like. It is understood by one of ordinary skill in the art that optical waveguides, optical fibers and fiber optic cables in general serve to transmit optical energy from one end to the other, with minimal loss and are therefore used interchangeably herein. These optical devices are not exclusive and other suitable optical devices may be used, as well.

As lesion forms in the tissue from ablation carried out by tip electrode 37 of the catheter 10, its characteristics are altered as understood by one of ordinary skill in the art. In particular, as the lesion is radiated by light, the light is scattered and/or reflected back toward the tip electrode 37, where such light having interacted or otherwise having been affected by the lesion bears qualitative and quantitative information about the lesion as it reenters the hollow cavity 49.

With its distal end inserted into the hollow cavity, the receiving optical fiber 43R collects recaptured light which bears the qualitative and quantitative information and is transmitted to an optical processing system, as described below in further detail. In accordance with a feature of the present invention, the tip section 36 serves as a generally omni-directional optical radiator and collector, as well as an ablation tip.

The present catheter may also be adapted for irrigation or infusion at the tip electrode, such as for cooling the tissue site and to improve electrical conduction for deeper and larger lesions. Fluid, e.g., saline, is fed into the hollow cavity by an irrigation tube segment 48, as shown in FIG. 5B. The distal end of the tube segment 48 is anchored in the passage 110 (FIG. 6) and extends proximally through the plastic housing 21, the fourth lumen 35 of the intermediate section 14 (FIG. 2A), the central lumen 18 of the catheter body 12, and through the control handle 16 where it terminates in a luer hub 90 (FIG. 1) or the like at a location proximal to the control handle. In practice, fluid may be injected by a pump (not shown) into the infusion tube 48 through the luer hub 90, and flows into the hollow cavity 49 in the tip electrode 37, and out the openings 87. The infusion tube 48 may be made of any suitable material, and is preferably made of polyimide tubing. A suitable infusion tube has an outer diameter of from about 0.32 inch to about 0.036 inch and an inner diameter of from about 0.28 inch to about 0.032 inch.

To energize the tip electrode 37, in particular the carbon nanotube film 39 for RF ablation, a lead wire 40 is provided. The lead wire 40 extends through the third lumen 34 of intermediate section 14 (FIG. 4), the central lumen 18 of the catheter body 12 (FIGS. 2A and 2B), and the control handle 16, and terminates at its proximal end in an input jack (not shown) that may be plugged into an appropriate monitor (not shown). The portion of the lead wire 40 extending through the central lumen 18 of the catheter body 12, control handle 16 and distal end of the intermediate section 14 is enclosed within a protective sheath 52, which can be made of any suitable material, preferably Teflon®. The protective sheath 52 is anchored at its distal end to the distal end of the intermediate section 14 by gluing it in the lumen 34 with polyurethane glue or the like.

In the disclosed embodiment, the carbon nanotube film 39 is energized by the lead wire 40 via a ring electrode 55 that is mounted to overlap a junction between the plastic housing 21 and the carbon nanotube film 39 on the shell 38 of the dome tip electrode 37, as shown in FIGS. 5A and 5B. The ring electrode can be made of any suitable solid conductive material, such as platinum or gold, preferably a combination of platinum and iridium, and mounted with glue or the like. Alternatively, the ring electrode can be formed by coating the junction with an electrically conducting material, like platinum, gold and/or iridium. The coating can be applied using sputtering, ion beam deposition or an equivalent technique. In another alternative embodiment, the ring electrode can be formed by repeatedly wrapping an end of the electrode lead wire around the junction and stripping off the coating of the lead wire to expose a conductive surface. Other methods for forming ring electrode can also be used in accordance with the invention. In the disclosed embodiment, the ring electrode is mounted by first forming a hole in the wall of the plastic housing 21. The electrode lead wire 40 is fed through the hole, and the ring electrode is welded in place over the lead wire and the carbon nanotube film 37.

A temperature sensing means is provided for the tip electrode 37 in the disclosed embodiment. Any conventional temperature sensing means, e.g., a thermocouple or thermistor, may be used. With reference to FIGS. 5B and 6, a suitable temperature sensing means for the tip electrode 37 comprises a thermocouple formed by a wire pair. One wire of the wire pair is a copper wire 41, e.g., a number 40 copper wire. The other wire of the wire pair is a constantan wire 45, which gives support and strength to the wire pair. The wires 41 and 45 of the wire pair are electrically isolated from each other except at their distal ends where they contact and are twisted together, covered with a short piece of plastic tubing 63, e.g., polyimide, and covered with epoxy. The plastic tubing 63 is then attached in the hole 104 of the plug 44, by epoxy or the like. As shown in FIGS. 2A and 5, the wires 41 and 45 extend through the second lumen 32 in the intermediate section 14. The wires 41 and 45 extend through the central lumen 18 of the catheter body 12 and the lumen 32 of the intermediate section 14 within the protective sheath 53. The wires 41 and 45 then extend out through the control handle 16 and to a connector (not shown) connectable to a temperature monitor (not shown). Alternatively, the temperature sensing means may be a thermistor. A suitable thermistor for use in the present invention is Model No. AB6N2-GC14KA143T/37C sold by Thermometrics (New Jersey).

Referring to FIGS. 2B and 3B, the puller wire 42 extends through the catheter body 12 and is anchored at its proximal end to the control handle 16. The puller wire is made of any suitable metal, such as stainless steel or Nitinol, and is preferably coated with Teflon® or the like. The coating imparts lubricity to the puller wire. The puller wire preferably has a diameter ranging from about 0.006 to about 0.010 inches. A compression coil 56 is situated within the catheter body 12 in surrounding relation to the puller wire. The compression coil 56 extends from the proximal end of the catheter body 12 to the proximal end of the intermediate section 14. The compression coil is made of any suitable metal, preferably stainless steel, and is tightly wound on itself to provide flexibility, i.e., bending, but to resist compression. The inner diameter of the compression coil is preferably slightly larger than the diameter of the puller wire 42. The Teflon® coating on the puller wire allows it to slide freely within the compression coil. If desired, particularly if the lead wire 40 is not enclosed by the protective sheath 52, the outer surface of the compression coils can be covered by a flexible, non-conductive sheath, e.g., made of polyimide tubing, to prevent contact between the compression coils and any other wires within the catheter body 12.

As shown in FIG. 2B, the compression coil 56 is anchored at its proximal end to the proximal end of the stiffening tube 20 in the catheter body 12 by glue joint 50 and at its distal end to the intermediate section 14 by glue joint 51. Both glue joints 50 and 51 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 22 of the catheter body 12 and the stiffening tube 20 which is heated sufficiently to form a permanent hole. The glue is then introduced through the hole to the outer surface of the compression coil 56 and wicks around the outer circumference to form a glue joint about the entire circumference of the compression coil.

With reference to FIGS. 3B and 4, the puller wire 42 extends into the first lumen 30 of the intermediate section 14. In the disclosed embodiment, the puller wire 42 is anchored at its distal end to a side wall of the plastic tubing 21. The distal end of the puller wire 42 comprises a T-bar anchor 61 and is anchored by glue in notch 63 in the side wall of the plastic housing 21 as shown in FIG. 3B. Such anchoring is described in U.S. Pat. No. 6,064,908, the entire disclosure of which is incorporated herein by reference. Within the first lumen 30 of the intermediate section 14, the puller wire 42 extends through a plastic, preferably Teflon®, sheath 81, which prevents the puller wire 42 from cutting into the wall of the intermediate section 14 when the intermediate section is deflected. Longitudinal movement of the puller wire 42 relative to the catheter body 12, which results in deflection of the tip section 36, is accomplished by suitable manipulation of the control handle 16. Suitable control handles are described in U.S. Pat. No. 6,602,242, the entire disclosure of which is hereby incorporated by reference.

In the illustrated embodiment, the tip section 36 carries an electromagnetic sensor 72, and as mentioned, the electromagnetic sensor may be carried in the plastic housing 21, with its distal end anchored in the blind hole 106 in the plug 44 as shown in FIGS. 5A, 5B and 6. The electromagnetic sensor 72 is connected to an electromagnetic sensor cable 74. As shown in FIGS. 2A and 4, the sensor cable 74 extends through the fourth lumen 35 of the tip section 36, through the central lumen 18 of the catheter body 12, and into the control handle 16. The electromagnetic sensor cable 74 then extends out the proximal end of the control handle 16 within an umbilical cord 78 (FIG. 1) to a sensor control module 75 that houses a circuit board (not shown). Alternatively, the circuit board can be housed within the control handle 16, for example, as described in U.S. patent application Ser. No. 08/924,616, entitled "Steerable Direct Myocardial Revascularization Catheter", the disclosure of which is incorporated herein by reference. The electromagnetic sensor cable 74 comprises multiple wires encased within a plastic covered sheath. In the sensor control module 75, the wires of the electromagnetic sensor cable 74 are connected to the circuit board. The circuit board amplifies the signal received from the electromagnetic sensor 72 and transmits it to a computer in a form understandable by the computer by means of the sensor connector 77 at the proximal end of the sensor control module 75, as shown in FIG. 1. Because the catheter can be designed for single use only, the circuit board may contain an EPROM chip which shuts down the circuit board approximately 24 hours after the catheter has been used. This prevents the catheter, or at least the electromagnetic sensor, from being used twice. Suitable electromagnetic sensors for use with the present invention are described, for example, in U.S. Pat. Nos. 5,558,091, 5,443, 489, 5,480,422, 5,546,951, 5,568,809, and 5,391,199 and International Publication No. WO 95/02995, the disclosures of which are incorporated herein by reference. An electromagnetic mapping sensor 72 may have a length of from about 6 mm to about 7 mm and a diameter of about 1.3 mm.

Figure 7:
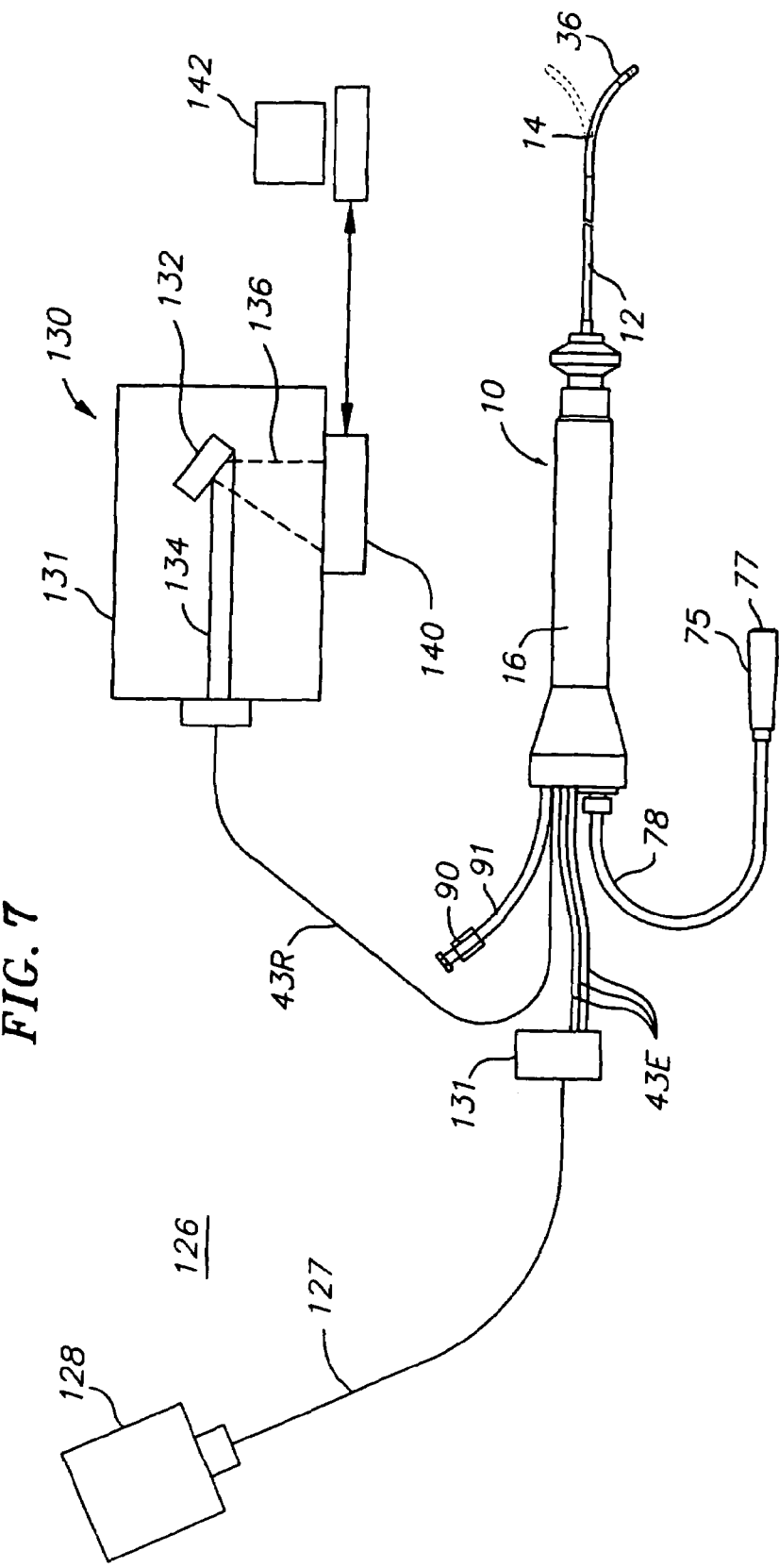
FIG. 7 is a schematic drawing showing components of an embodiment of an optical processing system for use with the catheter of the present invention.

With reference to FIG. 7, an optical processing system 126 for optically evaluating ablation tissue using the catheter 10 is illustrated. A light source 128 supplies a broadband (white; multiple wavelengths) light and/or laser light (single wavelength) radiation to the tip section 36 of the catheter 10 via cable 127 which is split by a beamsplitter 131 outputting to the emitting cables 43E. The light bearing lesion qualitative information from the tip section is transmitted by the receiving cable 43R to a detection component 130. The detection component may comprise, for example, a wavelength selective element 131 that disperses the collected light into constituent wavelengths, and a quantification apparatus 140. The at least one wavelength selective element 131 includes optics 132, as are known in the art, for example, a system of lenses, mirrors and/or prisms, for receiving incident light 34 and splitting it into desired components 136 that are transmitted into the quantification apparatus 140.

The quantification apparatus 140 translates measured light intensities into an electrical signal that can be processed with a computer 142 and displayed graphically to an operator of the catheter 10. The quantification apparatus 140 may comprise a charged coupled device (CCD) for simultaneous detection and quantification of these light intensities. Alternatively, a number of different light sensors, including photodiodes, photomultipliers or complementary metal oxide semiconductor (CMOS) detectors may be used in place of the CCD converter. Information is transmitted from the quantification device 140 to the computer 142 where a graphical display or other information is generated regarding parameters of the lesion. A suitable system for use with the catheter 10 is described in U.S. application Ser. No. 11/281,179, the entire disclosure of which is hereby incorporated by reference.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter, comprising:
   a catheter body;
   a tip electrode with an optically transmissive shell and a carbon nanotube film on said shell; and
   a ring electrode at least partially mounted on the film of the tip electrode, the ring electrode being electrically connected to the film.

2. A catheter of claim 1, wherein the optically transmissive shell is adapted for optical illumination and collection, and the carbon nanotube film is adapted for tissue ablation.

3. A catheter of claim 1, wherein the shell is generally shaped as a dome.

4. A catheter of claim 1, wherein the shell is optically transparent.

5. A catheter of claim 1, wherein the film is optically transmissive.

6. A catheter of claim 1, wherein the film is optically transparent.

7. A catheter of claim 1, wherein the tip electrode is illuminated by at least one emitting optical fiber.

8. A catheter of claim 1, wherein light entering the tip electrode from tissue is received by at least one receiving optical fiber.

9. A catheter of claim 8, wherein the receiving optical fiber transmits the light entering the tip electrode to an optical processing system.

10. A catheter of claim 1, wherein the shell defines a cavity from which light illuminates tissue and into which light from tissue is received by the tip electrode.

11. A catheter adapted to ablate tissue, comprising:
    a catheter body;
    a tip electrode distal the catheter body, the tip electrode having an optically transparent shell and an electrically conductive and optically transparent carbon nanotube film on the shell, the shell defining a cavity to receive light from the tissue and the film being adapted to ablate tissue;
    a ring electrode at least partially mounted on the film of the tip electrode, the ring electrode being electrically connected to the film;
    a first optical waveguide extending into the cavity to provide light into the cavity; and
    a second optical waveguide extending into the cavity to collect light in the cavity.

12. A catheter of claim 11, wherein the tip electrode is adapted for RF ablation.

13. A catheter of claim 11, further comprising an irrigation tubing configured to pass fluid that enters the cavity and passes through openings formed in the shell to exit the tip electrode.

14. A catheter of claim 11, further comprising a deflectable intermediate section between the catheter body and the tip electrode.

15. A catheter of claim 11, further comprising a temperature sensor configured to sense temperature in the tip electrode.

16. A catheter of claim 11, further comprising an electromagnetic location sensor configured to sense a location of the tip electrode.

* * * * *